(12) United States Patent
Oh

(10) Patent No.: US 9,378,547 B2
(45) Date of Patent: Jun. 28, 2016

(54) IMAGE DISTORTION COMPENSATION DEVICE, MEDICAL IMAGING DEVICE COMPRISING THE SAME AND METHOD FOR COMPENSATING IMAGE DISTORTION

(71) Applicant: Samsung Electronics Co., Ltd., Gyeonggi-do (KR)

(72) Inventor: Jung Teak Oh, Seoul (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 288 days.

(21) Appl. No.: 13/916,841

(22) Filed: Jun. 13, 2013

(65) Prior Publication Data

US 2014/0002475 A1    Jan. 2, 2014

(30) Foreign Application Priority Data

Jun. 27, 2012    (KR) .......................... 10-2012-0069189

(51) Int. Cl.
| | | |
|---|---|---|
| G09G 5/02 | (2006.01) | |
| G06T 7/00 | (2006.01) | |
| A61B 6/00 | (2006.01) | |
| A61B 8/00 | (2006.01) | |
| A61B 5/00 | (2006.01) | |
| A61F 9/02 | (2006.01) | |
| A61B 6/10 | (2006.01) | |

(52) U.S. Cl.
CPC .............. *G06T 7/0012* (2013.01); *A61B 5/0095* (2013.01); *A61B 6/461* (2013.01); *A61B 8/461* (2013.01); *A61F 9/022* (2013.01); *G09G 5/02* (2013.01); *A61B 6/107* (2013.01); *G09G 2320/0242* (2013.01); *G09G 2380/08* (2013.01)

(58) Field of Classification Search
None
See application file for complete search history.

(56) References Cited

U.S. PATENT DOCUMENTS

| | | | |
|---|---|---|---|
| 2002/0039104 A1* | 4/2002 | Sato et al. ..................... 345/600 |
| 2005/0024583 A1 | 2/2005 | Neuberger | |
| 2007/0195181 A1* | 8/2007 | Onomura ...................... 348/272 |
| 2009/0033676 A1* | 2/2009 | Cybart ................. G09G 3/2003 345/589 |
| 2010/0302273 A1* | 12/2010 | Myers .................. G09G 3/2096 345/593 |
| 2012/0075435 A1* | 3/2012 | Hovanky et al. ................ 348/51 |
| 2012/0176373 A1* | 7/2012 | Haga .................. H04N 13/0007 345/419 |
| 2013/0141432 A1* | 6/2013 | Wang et al. .................... 345/419 |
| 2014/0340287 A1* | 11/2014 | Achilefu et al. .................. 345/8 |

FOREIGN PATENT DOCUMENTS

| | | |
|---|---|---|
| JP | 2005-130360 A | 5/2005 |
| JP | 2010-119654 A | 6/2010 |
| KR | 10-2005-0034092 A | 4/2005 |
| WO | 2006/073408 A2 | 7/2006 |
| WO | WO 2006073408 A2 * | 7/2006 |

* cited by examiner

*Primary Examiner* — Phi Hoang
*Assistant Examiner* — Diane Wills
(74) *Attorney, Agent, or Firm* — Cha & Reiter, LLC

(57) ABSTRACT

Disclosed is an image distortion compensation device which enables user to perceive a medical image having reduced or eliminated image distortion while wearing color-filtered safety goggles. The device corrects colors of a medical image displayed on a display unit using spectral characteristics of the safety goggles. A spectrometer may be included to measure the spectral characteristics of the safety goggles.

24 Claims, 20 Drawing Sheets
(8 of 20 Drawing Sheet(s) Filed in Color)

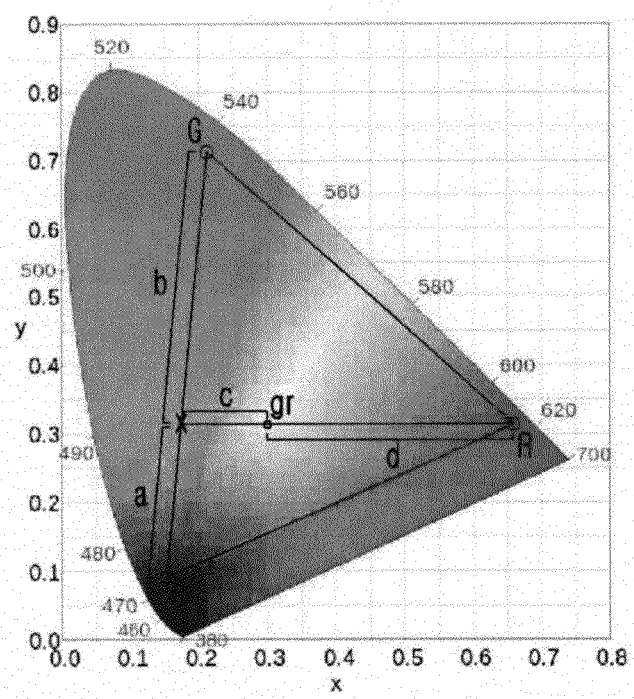

100"

IMAGE DISTORTION COMPENSATION DEVICE, MEDICAL IMAGING DEVICE COMPRISING THE SAME AND METHOD FOR COMPENSATING IMAGE DISTORTION

CLAIM OF PRIORITY

This application claims the benefit under 35 U.S.C. §119(a) of Korean Patent Application No. 10-2012-0069189, filed on Jun. 27, 2012, in the Korean Intellectual Property Office, the disclosure of which is incorporated herein by reference.

BACKGROUND

1. Technical Field

The present disclosure relates generally to image compensation techniques and more particularly to an image distortion compensation device for compensating image distortion caused by color-filtered safety goggles.

2. Description of the Related Art

A medical imaging device acquires an image of a subject using transmission, absorption or reflection properties of ultrasonic waves, lasers, X-rays or the like with respect to the subject, and uses the image for diagnosis. Examples of imaging devices include ultrasonic, photoacoustic, and X-ray imaging devices.

Some medical imaging devices require that safety goggles be worn to protect the eyes of both an inspector and a subject. In particular, with photoacoustic imaging, a laser having a nano-scaled short wavelength is irradiated during a procedure; thus it is typically necessary for all participants involved to wear safety goggles to protect their eyes.

Since safety goggles absorb light with a specific wavelength, image distortion occurs on an image passing through the safety goggles. When the inspector views a medical image while wearing safety goggles, a difference occurs between an actually displayed medical image and the medical image seen from the vantage point of the inspector.

Accordingly, the inspector wearing safety goggles does not perceive the medical image accurately. Thus a need exists to alleviate this disadvantage.

SUMMARY

Embodiments described herein provide an image distortion compensation technique which enables a user to view a medical image having minimal or eliminated image distortion while wearing color-filtered safety goggles, by correcting colors of a medical image displayed on a display unit using spectral characteristics of the safety goggles.

In an exemplary embodiment, an image distortion compensation device for compensating image distortion on an image traversing safety goggles includes an image distortion estimation unit to estimate image distortion based on spectral characteristics of the safety goggles. A color correction unit performs color correction to compensate the estimated image distortion with respect to an image to be displayed on a display unit.

In various embodiments:

The spectral characteristics of the safety goggles may include light absorbance of the safety goggles according to wavelength.

The image distortion estimation unit may determine whether or not compensation of image distortion is possible through the color correction.

The image distortion estimation unit may determine that compensation of image distortion is impossible through the color correction when, among colors used for an image to be displayed on the display unit, a color not represented in an image to which light absorption effects of the safety goggles are applied is present.

The image distortion compensation device may further include a color mapping unit to substitute the color not represented in the image to which light absorption effects of the safety goggles, among the colors used for the image displayed on the display unit, by a color represented in the image to which light absorption effects of the safety goggles are applied.

The image distortion compensation device may further include a storage unit to store at least one spectral characteristic of the safety goggles.

The image distortion estimation unit may estimate image distortion using a selected one of more of the spectral characteristics stored in the storage unit.

The image distortion estimation unit may estimate coordinate change of primary colors by absorption effects of the safety goggles, and the coordinates of primary colors may include coordinates in a color space used for the display unit.

The color correction unit may control a synthesis ratio of primary colors to realize a specific color included in the image displayed on the display unit, based on the estimated coordinates of primary colors.

The image distortion compensation device may further include a spectrometer to measure the spectral characteristics of the safety goggles.

In accordance with a further aspect of the present invention, a medical imaging device includes the image distortion compensation device.

The medical imaging device may include a display unit, wherein the display unit displays a photoacoustic image or a photoacoustic/ultrasonic image of an object.

The display unit may display an image color-corrected by the color correction unit or an image color-mapped by the color mapping unit.

The medical imaging device may further include an input unit to input selection of a substituted color from the color mapping unit.

The medical imaging device may further include an input unit to input selection of at least one of spectral characteristics of the safety goggles stored in the storage unit.

Exemplary methods operable in the image distortion compensation device and medical imaging device are also disclosed.

BRIEF DESCRIPTION OF THE DRAWINGS

The patent or application file contains at least one drawing executed in color. Copies of this patent or patent application publication with color drawings will be provided by the U.S. Patent and Trademark Office upon request and payment of the necessary fee.

These and/or other aspects of the invention will become apparent and more readily appreciated from the following description of the embodiments, taken in conjunction with the accompanying drawings, in which like reference numerals are used for like elements, of which:

FIG. 5A is a chromaticity diagram illustrating a coordinate of gray in a CIE 1931 color space;

DETAILED DESCRIPTION

Hereinafter, embodiments of the present invention will be described with reference to the accompanying drawings.

Herein, the term "distortion" refers to color distortion, contrast distortion, or other type of distortion, depending on the context of use.

Herein, terms such as " . . . unit" or "module," disclosed in the specification indicates a unit for performing at least one function or operation, and this may be implemented by hardware or a combination of hardware and software.

As used herein, an element or step recited in the singular and proceeded with the word "a" or "an" should be understood as not excluding plural of the elements or steps, unless such exclusion is explicitly stated. Furthermore, references to "one embodiment" or "an embodiment" are not intended to be interpreted as excluding the existence of additional embodiments that also incorporate the recited features. Moreover, unless explicitly stated to the contrary, embodiments "comprising", "including" or "having" an element or a plurality of elements with a particular property may include additional such elements not having that property.

Ultrasonic imaging is widely used as a medical imaging method for diagnosing a subject. In recent years, photoacoustic imaging in which ultrasonic properties of an object (within a subject) is combined with photoacoustic properties thereof has been developed and utilized in a variety of diagnosis fields.

Photoacoustic imaging (PAI) is a method in which an ultrasonic image having a high spatial resolution is combined with an optical image having a high contrast ratio suitable for imaging biological tissues. When a laser is irradiated to biological tissues, a short electromagnetic pulse of the laser is absorbed in the biological tissues and a momentary acoustic pressure is generated by thermo-elastic expansion in tissue sites acting as a generation source of an initial ultrasonic wave. The ultrasonic waves thus formed reach the surface of the biological tissues with various delays and a photoacoustic image is obtained by imaging the same.

Ultrasonic imaging is an established medical imaging method which diagnoses lesions of the human body using ultrasonic waves. An ultrasonic image may include a B-mode image to display a cross-sectional image of an object, an elasticity image showing elasticity information of the object, an M-mode image showing biological information of a specific part of the object, or a color doppler image to visualize the bloodstream in real-time.

Also, photoacoustic/ultrasonic imaging in which photoacoustic imaging is combined with ultrasonic imaging has recently been developed and used.

Figure 1:
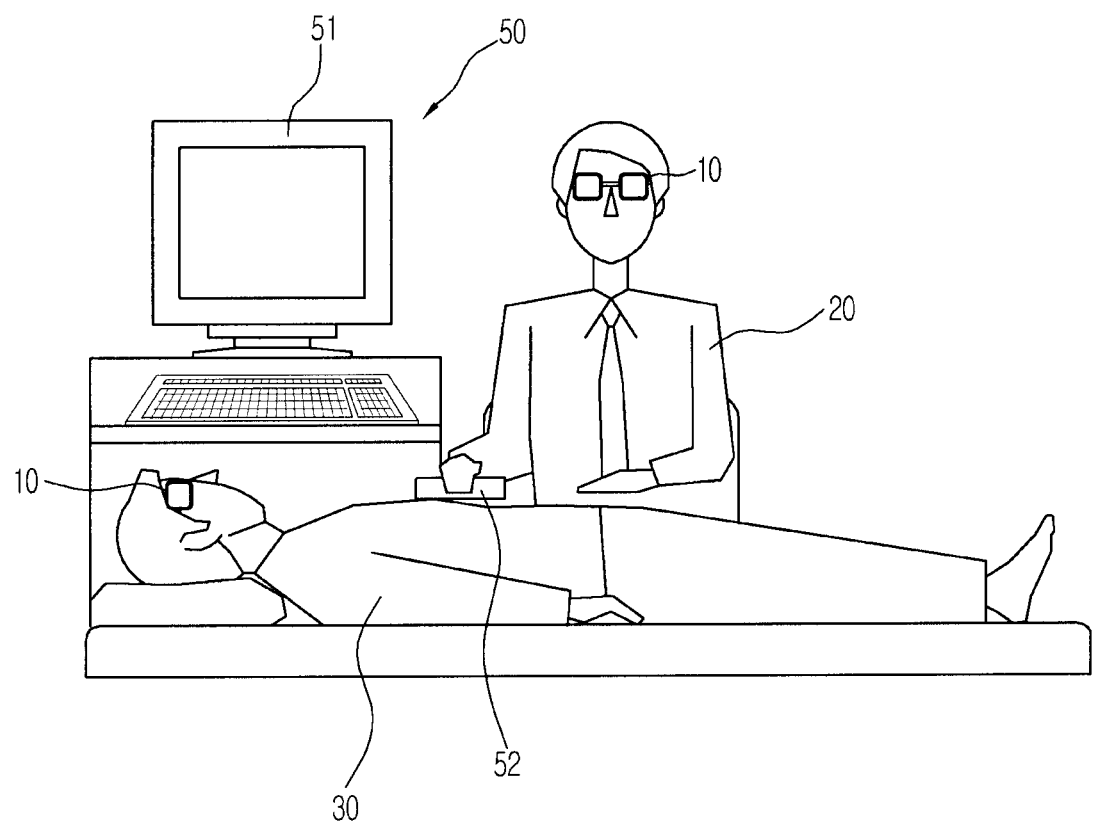
FIG. 1 illustrates a system for diagnosis of a subject using photoacoustic imaging or photoacoustic/ultrasonic imaging according to an embodiment.

FIG. 1 illustrates a system for diagnosis of a subject using photoacoustic imaging or photoacoustic/ultrasonic imaging according to an embodiment. In order to acquire a photoacoustic image, it is necessary to irradiate a laser with a considerably short wavelength to a subject 30. However, damage to optic nerves may occur if this laser is directly exposed to the eyes. Accordingly, when the subject 30 is diagnosed using a medical imaging device 50 such as a photoacoustic imaging device or photoacoustic/ultrasonic imaging device, both an inspector 20 and the subject 30 need to wear safety goggles 10.

Safety goggles 10 protect the eyes from a laser irradiated from a laser irradiator 52 by blocking the irradiated laser and preventing the same from reaching the eyes. Accordingly, the safety goggles 10 are designed to absorb light in a specific wavelength range; particular goggles are selected depending on the wavelength of the irradiated laser. For example, when a laser corresponds to a visible ray region having a wavelength shorter than green, the safety goggles may be designed to absorb light with a wavelength shorter than 532 nm. When a laser corresponds to red and infrared regions, the safety goggles may be designed to absorb light with a wavelength of 600 nm or more.

Medical imaging device 50 displays a medical image through a display unit 51. The display unit 51 may display a medical image using an RGB model, a CMYK model, or another suitable model. With the RGB model, a medical image is displayed through additive synthesis of primary colors, i.e., red (R), green (G) and blue (B). Color represented on the display unit 51 may be defined in various color spaces, for example, the CIE 1931 color space established by the Commission International de l'Eclairage (CIE).

Figure 2:
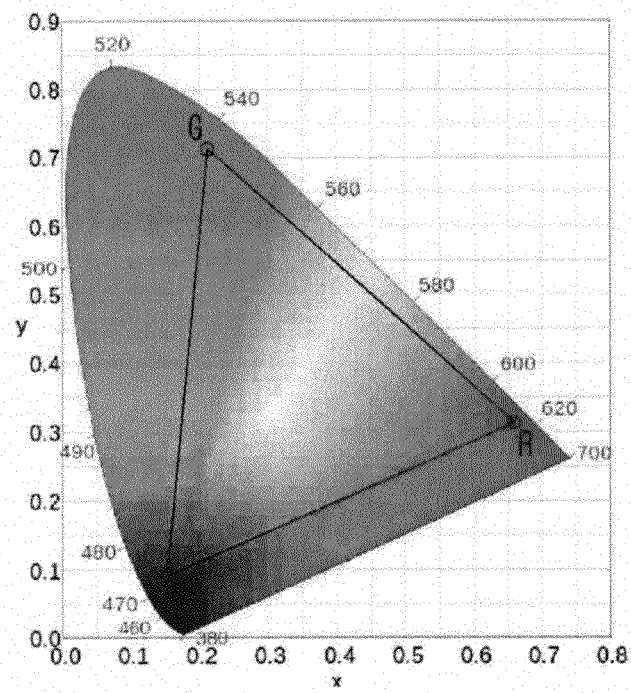
FIG. 2 is an example of a chromaticity diagram showing colors represented on a display unit of a medical imaging device.

FIG. 2 is an example of a chromaticity diagram showing color represented on a display unit 51 in the medical imaging device 50. The color may be represented by various chromaticity diagrams, e.g., by a CIE 1931 chromaticity diagram for the case of CIE 1931 color space.

CIE 1931 color space is also called "CIE XYZ color space", where X, Y and Z represent trichromatic stimulus values which are similar to values indicating red, green and blue levels. The concept of color is divided into two factors, i.e., brightness and chromaticity. The CIE XYZ color space may be designed such that the value Y represents brightness. Accordingly, chromaticity of the color may be represented by the values x and y calculated by the following Equation 1.

$$x = X/(X+Y+Z)$$

$$y = Y/(X+Y+Z) \quad \text{eqn. (1)}$$

The chromaticity diagram of the CIE 1931 color space drawn using x and y is the chromaticity diagram shown in FIG. 2. Here, an outer curved boundary corresponds to monochromatic lights, and the wavelengths of the monochromatic lights are measured in nanometers.

Generally, it is impossible for the display unit to represent all colors represented in the CIE 1931 chromaticity diagram. A color range that is represented is referred to as a color gamut. For example, as shown in FIG. 2, the color gamut may correspond to a triangular inner space having R (0.675, 0.325), G (0.285, 0.595) and B (0.154, 0.068). These represent coordinates of red (R), green (G) and blue (B) as vertexes, which means that the display unit displays colors within the RGB triangle.

Hereinafter, an operation of an image distortion compensation device according to embodiments of the present invention will be described in detail based on the afore-mentioned information.

Figure 3:
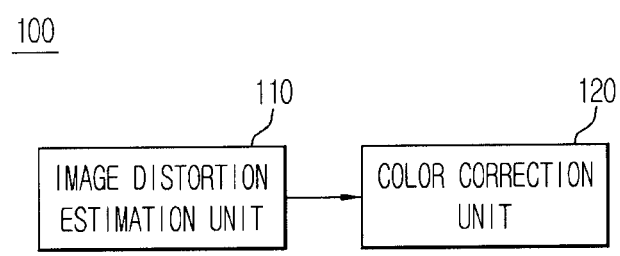
FIG. 3 is a block diagram illustrating a configuration of an image distortion compensation device according to one embodiment of the present invention.

FIG. 3 is a block diagram illustrating a configuration of an image distortion compensation device, 100, according to one embodiment of the present invention. Device 100 includes an image distortion estimation unit 110 to estimate image distortion caused by wearing of safety goggles 10, and a color correction unit 120 to at least preliminarily compensate the estimated image distortion. Each of the units described herein such as units 110 and 120 can be embodied with at least one processor and a memory to execute the respective functions. Alternatively, a single processor and memory may be shared between some or all of the units of a described device to execute the respective functions by reading respective software programs from the memory and executing the programs on the processor.

The image distortion estimation unit 110 estimates image distortion which may occur when an image displayed on the display unit 51 passes through (i.e., "traverses") the safety goggles. Estimation is done on the basis of spectral characteristics of the safety goggles 10 and spectral characteristics of the display unit 51, both of which may be input by a designer or a user. When the image distortion compensation device 100 is incorporated in the medical imaging device 50, it may automatically obtain spectral characteristics of the display unit 51.

The type of safety goggles used depends on the wavelength of the laser generated in the medical imaging device; for a laser having a wavelength shorter than green, safety goggles blocking light of wavelength shorter than 532 nm are used. For a laser having a red or infrared region, the safety goggles are designed to block light of wavelength 600 nm or more. For convenience of description in explaining the following embodiments, a case in which the medical imaging device 50 generates a laser with a red region will be described.

Figure 4A:
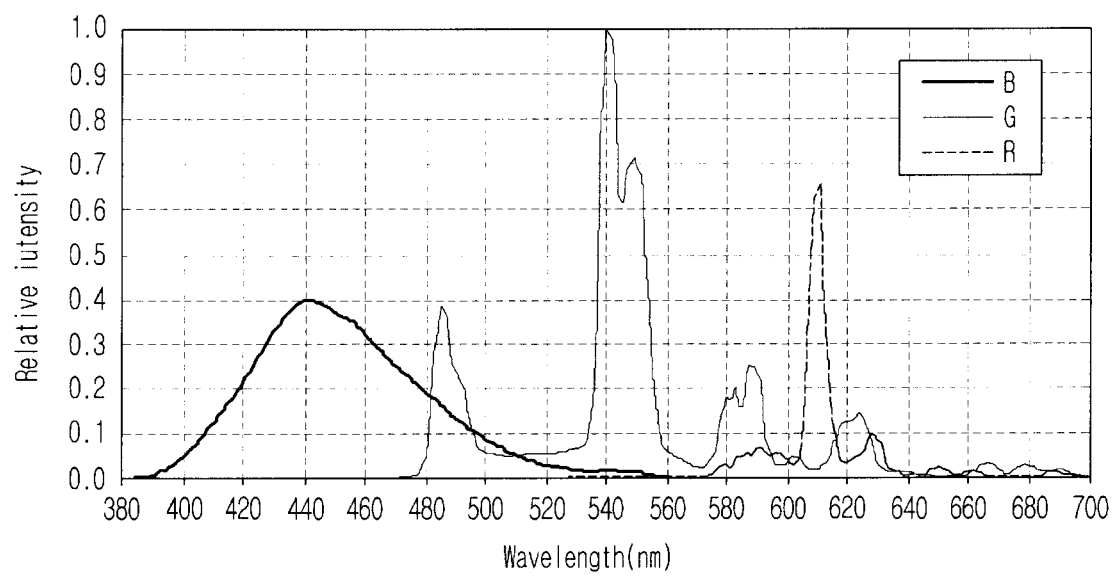
FIG. 4A is a graph showing example spectral characteristics of the display unit.
Figure 4B:
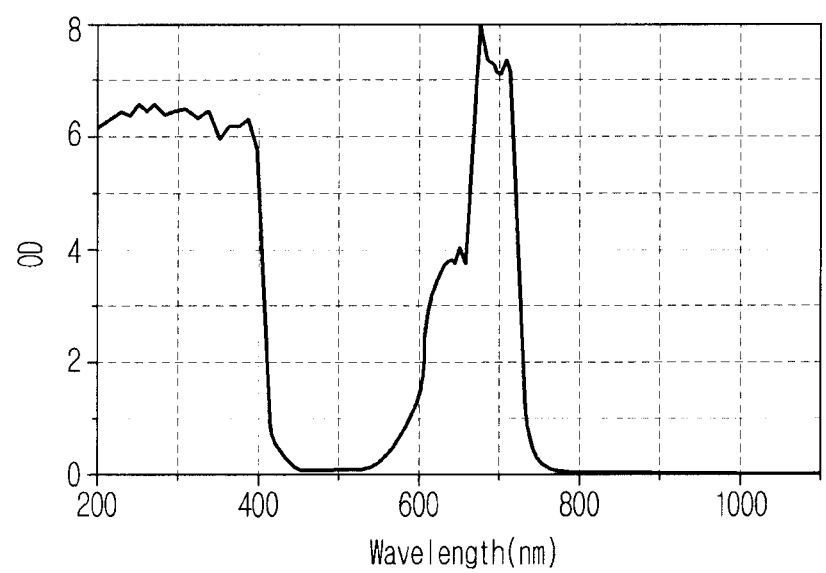
FIG. 4B is a graph showing example spectral characteristics of safety goggles.

FIG. 4A is a graph showing example spectral characteristics of a display unit, and FIG. 4B is a graph showing example spectral characteristics of safety goggles. The safety goggles having spectral characteristics of FIG. 4B are safety goggles which block or absorb light within a red region.

Referring to FIG. 4A, to display an image, the display unit emits light within a visible region (about 380 nm to 700 nm) which corresponds to a light region visible to humans. In general, the spectral characteristics depend on the type of the display unit. The spectral characteristics shown in FIG. 4A are those of a projection-type CRT display unit. The graph of FIG. 4B shows an optical density indicating transmittance of light, illustrating spectral characteristics of the safety goggles. The optical density is defined according to the following Equation 2.

$$OD = \log_{10}(l_{in}/l_{out}) \quad \text{eqn. (2)}$$

where OD represents optical density, $l_{in}$ represents intensity of incident light, and $l_{out}$ represents an intensity of a transmitted light. Optical density, which is also called absorbance, increases as light attenuation increases.

In the example of FIG. 4B, the optical density is considerably high in a region ranging from about 680 nm to about 710 nm. This means that the safety goggles having spectral characteristics of FIG. 4B have high absorbance with respect to light in the red region. Accordingly, when an inspector wears the safety goggles having spectral characteristics of FIG. 4B, the laser within a red region is blocked by the safety goggles and his eyes are thus protected, while at the same time, light within a red region emitted from the display unit is also blocked. That is, the image displayed on the display unit appears distorted in terms of color from the vantage point of the inspector.

The CIE 1931 color space and the CIE 1931 chromaticity diagram will be described as examples in embodiments described below for convenience of description. In alternative embodiments, image distortion can be compensated using other color spaces.

In general, a medical image is usually represented by a black-and-white image; this black-and-white image can be generated with an RGB-based color display unit through additive synthesis of the three primary colors (red, green, blue). In an embodiment described below, the black-and-white image renders gray through additive synthesis of three primary colors, and black and white is rendered by controlling brightness (luminance) of gray.

Figure 5B:
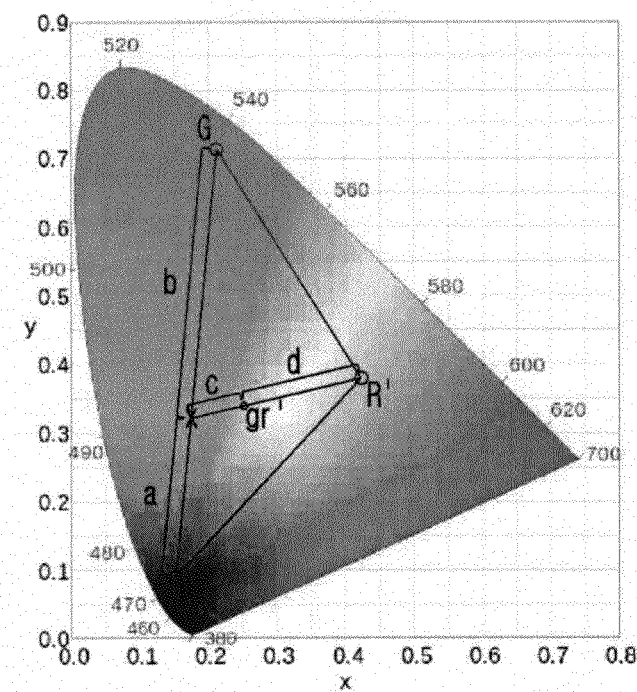
FIG. 5B is a chromaticity diagram showing change in coordinates caused by wearing of the safety goggles.

FIG. 5A is a chromaticity diagram illustrating a coordinate of gray on a CIE 1931 color space. FIG. 5B is a chromaticity diagram showing change in coordinate as observed by a user, caused by wearing of the safety goggles.

Referring to FIG. 5A, when the coordinate "gr" on the chromaticity diagram renders gray, the display unit maintains a division ratio (a:b) of a BG straight line, and a division ratio (c:d) of an XR straight line and changes brightness to render a black-and-white image. Such a division ratio is referred to as additive synthesis ratio. (The location of X is determined by extending a straight line drawn from the R point to the gray point gr.)

However, when the image displayed on the display unit 51 traverses the safety goggles having spectral characteristics of FIG. 4B, that is, an inspector sees the display unit 51 while wearing the safety goggles, light within a red region is partially blocked, as shown in FIG. 5B, and the red coordinate among the three primary colors is changed from R (0.675, 0.325) to R' (0.430, 0.40).

Accordingly, when the additive synthesis ratios, a:b and c:d, are maintained, the coordinate of gray is changed from gr to gr', and gray shown on the display unit 51 is seen by the inspector as another color having the coordinate gr'. (The values of c and d in FIG. 5B differ from those of FIG. 5A but the c:d ratio is the same. The values of a and b, and the location of X, are the same in both figures.) For this reason, the black-and-white image seen through the safety goggles is distorted.

The image distortion estimation unit 110 estimates image distortion shown in FIG. 5B using the spectral characteristics of the display unit 51 and spectral characteristics of the safety goggles 10. Specifically, when the display unit displaying the black-and-white image has spectral characteristics shown in FIG. 4B and the safety goggles to be worn have spectral characteristics shown in FIG. 4A, the image distortion of FIG. 5B may be estimated from the image displayed on the display unit using absorbance properties of the safety goggles.

Also, the color correction unit 120 preliminarily performs color correction to compensate an estimated image distortion of the image to be displayed on the display unit, thereby preventing distortion from being observed while the image is viewed through the safety goggles 10.

Figure 6:
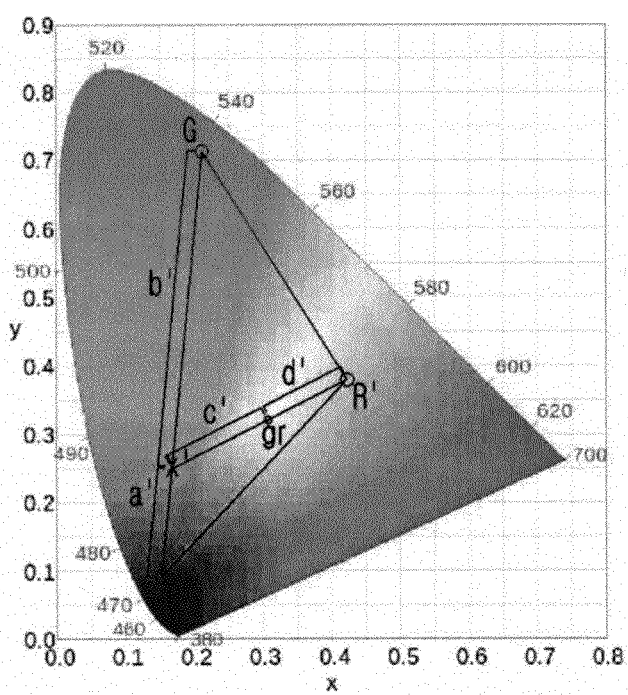
FIG. 6 is a chromaticity diagram illustrating change in the coordinate gr, when color correction is performed by a color correction unit.

FIG. 6 is a chromaticity diagram illustrating change in the coordinate gr, when a color correction unit 120 performs color correction.

As described in FIG. 5B above, when the additive synthesis ratio is maintained, the coordinate gr showing gray in the image displayed on the display unit 51 has a different value (of gr') in the image seen through the safety goggles 10 and is thus not seen as gray by the inspector. Accordingly, the color correction unit 120 controls the additive synthesis ratio, based on the coordinate R' estimated in the image distortion estimation unit 110 to prevent image distortion from being experienced by the inspector wearing the safety goggles 10.

Referring to FIG. 6, the color correction unit 120 changes the additive synthesis ratios to represent gray from a:b to a':b', and from c:d to c':d', with respect to the image represented on the display unit 51. When the additive synthesis ratios are controlled as described above, and a coordinate red is changed to R' through absorption of the safety goggles 10, the coordinate produced by additive synthesis is arranged at the same position (gr) as in FIG. 4A, indicating gray. In this manner, image distortion is not observed in the view through the safety goggles 10. In FIG. 6, a line drawn from R' to gr is extended to intersect the BG line at location of X'. The ratio a':b' is established relative to X', gr and R'. The ratio a':b' is established relative to X', B and G.

In brief, the image distortion estimation unit 110 estimates coordinate change of at least one of the three primary colors by applying absorption properties of the safety goggles 10 to the image displayed on the display unit 51. The color correction unit 120 determines a ratio to create a specific color through additive synthesis from the changed coordinates of the three primary colors and applies the determined additive synthesis ratio to the image displayed on the display unit. When the image displayed on the display unit 51 is a black-and-white image, the specific color is gray.

More specifically, conventionally, the display unit 51 displays a black-and-white image, i.e., a grayscale (monochromatic) image, which has the appearance of a color image to the viewer wearing the safety goggles. To generate the grayscale image on a color display, equal intensity of R, G and B is applied to each pixel of the display, but the intensities of each pixel are allowed to differ in order to generate contrast within the image. In the current embodiment, the actual image displayed on display unit 51 is changed from a grayscale image to a color image. This is done by applying, for a given pixel, a different amount of intensity to at least one of the R, G and B pixel elements. In the current example, the R pixel element of each pixel would be provided with higher intensity to compensate for the red wavelength filtering property of the safety goggles. Thus without the safety goggles, the compensated image displayed on display unit 51 would appear reddish.

The display unit 51 displays an image in which an additive synthesis ratio is controlled by the color correction unit 120, that is, a color-corrected image, and the color-corrected image does not exhibit distortion (or exhibits reduced distortion) from a vantage point of a viewer wearing the safety goggles.

In the embodiments described with reference to FIGS. 5A, 5B and 6, the image distortion compensation device compensates distortion shown on the black-and-white image. However, in other applications, a medical image is displayed as a color image such as a color doppler image. Hereinafter, an embodiment in which distortion of a color image is compensated will be described.

Figure 7A:
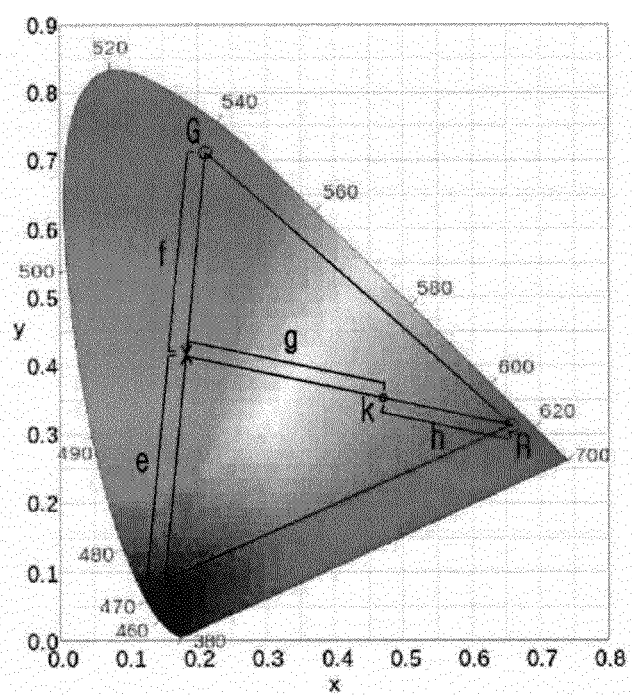
FIG. 7A is a chromaticity diagram illustrating a coordinate of a specific color in an image displayed on the display unit.
Figure 7B:
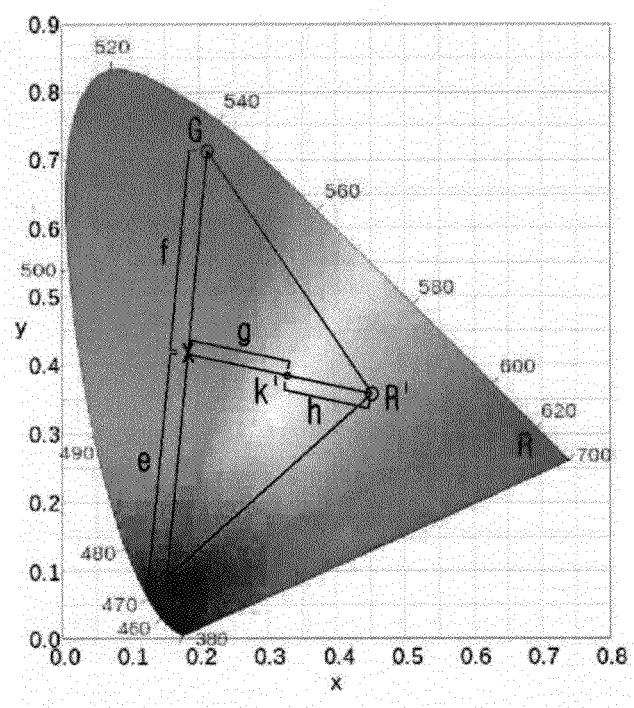
FIG. 7B is a chromaticity diagram illustrating change in coordinates due to absorption of light by the safety goggles.

FIG. 7A is a chromaticity diagram illustrating a coordinate of a specific color in an image displayed on the display unit. FIG. 7B is a chromaticity diagram illustrating a coordinate changed due to absorption of light by the safety goggles.

As shown in FIG. 7A, when color represented on the display unit is a color having a coordinate k, the color having the coordinate k is represented by e:f and g:h, additive synthesis ratios. When the display unit is seen through the safety goggles absorbing light in a red region, the color having a coordinate k is seen as a color that differs from the color actually displayed on the display unit. As shown in FIG. 7B, when the image displayed on the display unit traverses the safety goggles absorbing a red region, a coordinate of red among the three primary colors is changed to R' (i.e., the viewer sees less red) and the perceived coordinate in which the additive synthesis ratios are e:f and g:h is changed from k to k'. Accordingly, when the inspector views the display unit while wearing the safety goggles, image distortion occurs in which a color having the coordinate k displayed on the display unit is perceived as a color having a coordinate k'.

As described above, the image distortion estimation unit 110 estimates the image distortion shown in FIG. 7B using spectral characteristics of the display unit and spectral characteristics of the safety goggles. In an embodiment, by applying absorption properties of the safety goggles to the image displayed on the display unit, coordinate change of at least one of three primary colors is estimated.

The color correction unit 120 controls an additive synthesis ratio, based on the changed coordinates of three primary colors so that the color of light traversing the safety goggles becomes a color having the coordinate k.

Figure 8:
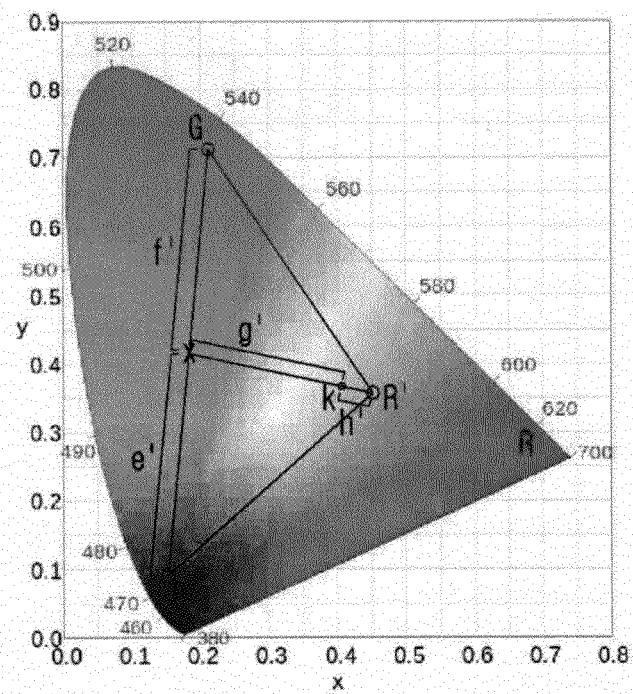
FIG. 8 is a chromaticity diagram illustrating change in the coordinate k when color correction is performed by the color correction unit.

FIG. 8 is a chromaticity diagram illustrating a change in coordinate k when color correction is performed by the color correction unit. Here, when the color correction unit 120 adjusts additive synthesis ratios to ei:f and g':h' and indicates the same on the display unit, color perceived through the safety goggles has the coordinate k, and a user wearing the safety goggles views an intended color to be displayed on the display unit. To realize this distortion compensation, the actual image displayed by the display unit 51 is modified by increasing intensities applied to the red pixel elements in the current example of red filtering safety goggles. That is, the actual image displayed is redder than the original image.

In the embodiments described above, the color correction unit 120 compensates image distortion through color correction by the color correction unit 120. However, when a region of light absorbed by the safety goggles is wide, there is a case in which compensation of image distortion through color correction is impossible, since a region of color which is represented in an image seen through the safety goggles is considerably narrow. Hereinafter, an image distortion compensation device useful for this case will be described below.

Figure 9:
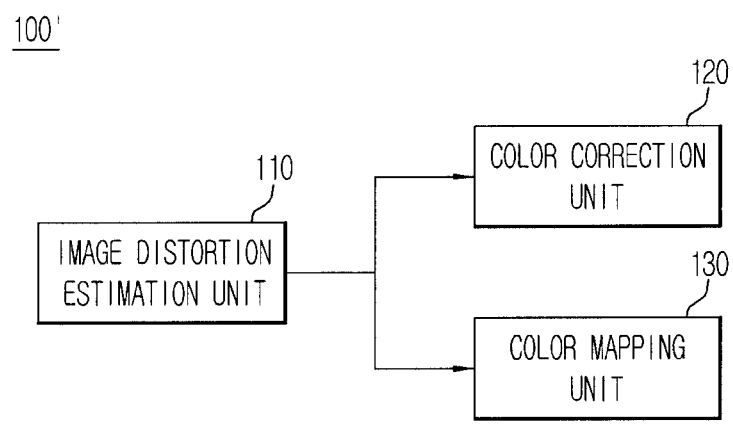
FIG. 9 is a block diagram illustrating an image distortion compensation device further including a color mapping unit.
Figure 10:
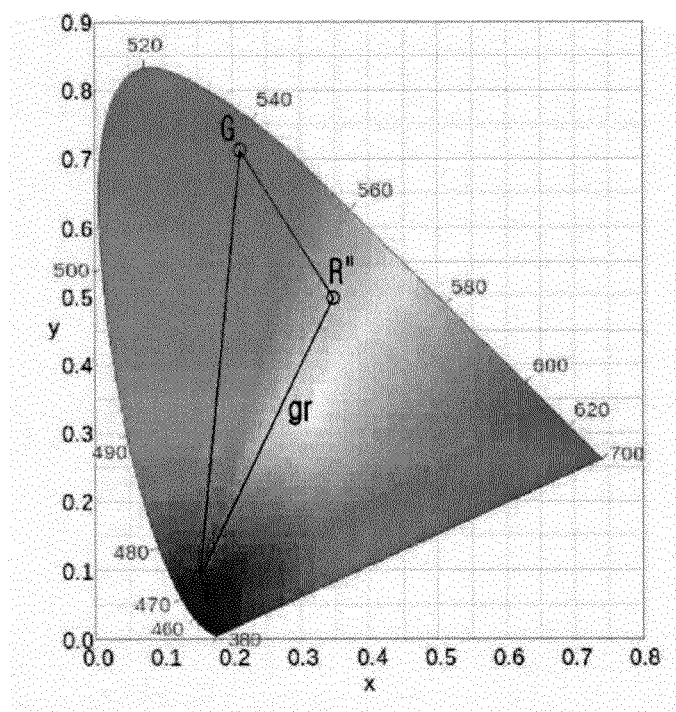
FIG. 10 is a chromaticity diagram illustrating a changed coordinate of gray after passing through the safety goggles.

FIG. 9 is a block diagram illustrating an image distortion compensation device further including a color mapping unit. FIG. 10 is a chromaticity diagram illustrating a coordinate of gray changed after passing through safety goggles.

Referring to FIG. 9, an image distortion compensation device 100' according to one embodiment of the present invention may further include a color mapping unit 130 to substitute a color represented in an image seen through the safety goggles by another color.

As in the embodiment described above, the image distortion estimation unit 110 estimates image distortion which may be generated in an image traversing the safety goggles using spectral characteristics of the safety goggles and spectral characteristics of the display unit. In the exemplary embodiments, although a coordinate of red among the three primary colors is changed from R to R' through light absorption by the safety goggles, the coordinate of color represented on the display unit falls within the triangle R'GB, corresponding to a range of color which may be represented by the image traversing the safety goggles.

However, in a case in which the safety goggles absorb light within a red region within a considerably wide range, as shown in FIG. 10, the coordinate of red among the three primary colors is shifted to R" and the coordinate "gr" indicating gray is disposed in an outer region of the triangle R"GB.

In this case, it is difficult to realize an image having colors created by combination of red and black-and-white with the image traversing the safety goggles. Accordingly, the image distortion estimation unit 110 determines whether a color that the display unit intends to display is represented in the image traversing the safety goggles, when color correction is performed. In an embodiment, in a case where the image displayed on the display unit is a black-and-white image, the image distortion estimation unit 110 determines whether or not the coordinate "gr" of gray is present in the triangle R"GB created by the changed coordinates of the three primary colors.

As a result of the determination of the image distortion estimation unit 110, when representation of an intended color is possible by color correction, the image distortion estimation unit 110 transmits a relevant command signal to the color correction unit 120 to allow the color correction unit 120 to perform color correction. However, when this is not possible, that is, when representation of an intended color is impossible by color correction, the image distortion estimation unit 110 transmits a relevant command signal to the color mapping unit 130.

When color correction is impossible, the color mapping unit 130 substitutes a color not represented in the image traversing the safety goggles by another color which may be represented. In an embodiment, for a case where an image displayed on the display unit is a black-and-white image and the image traversing the safety goggles is not a gray-scale image, the color mapping unit 130 maps other colors on the image displayed on the display unit, controls brightness of the mapped color and represents the image. The mapped other color is a color which may be represented in the image traversing the safety goggles.

Also, when the image to be displayed on the display unit contains red and the image traversing the safety goggles does not represent red (or represents substantially diminished red), the color mapping unit 130 maps a region corresponding to red in the image displayed on the display unit to another color which may be represented.

The image color-mapped in the color mapping unit 130 is displayed on the display unit 51 of the medical imaging device 50.

In some embodiments, when the image distortion compensation device 100' determines that the image to be displayed on the display unit 51 contains a color not represented in the image passing through the safety goggles, it informs a user of the impossibility of color correction through the display unit 51. Also, image distortion compensation device 100' indicates what color is represented. In this case, although the color mapping unit 130 does not perform color mapping, a user anticipates image distortion and analyzes an image without difficulty or confusion.

Also, the other (alternative) color mapped by the color mapping unit 130 is represented on the display unit 51 to inform the user of the alternative color. Alternatively, the color mapping unit 130 may receive selection of the alternative color from the user after informing of the same through the display unit 51 and then map the selected color to the color mapping unit 130. In the two cases, the user is better able to analyze the image without difficulty or confusion, even though the image displayed on the display unit 51 represents a color different from that of the original image.

Figure 11A:
FIGS. 11A and 11B are block diagrams illustrating respective configurations of an image distortion compensation device further including a storage unit.
Figure 11B:
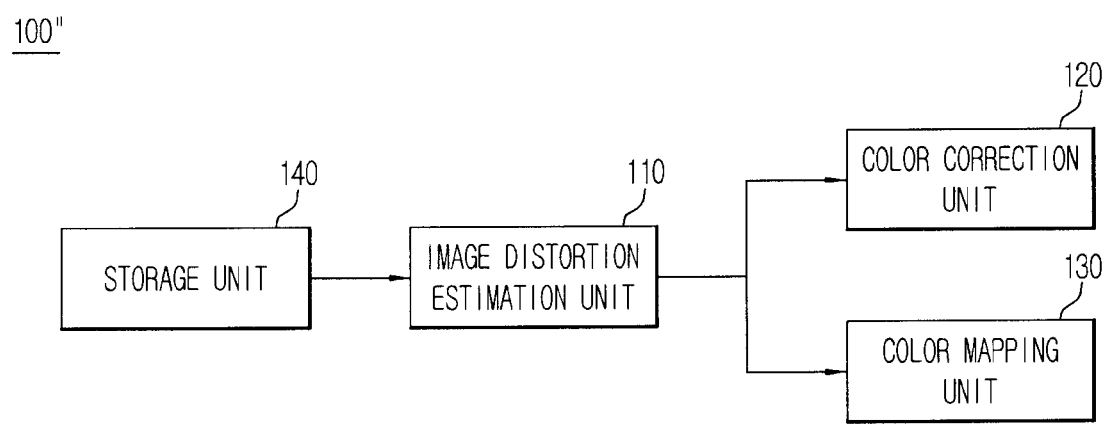

FIGS. 11A and 11B are block diagrams illustrating respective configurations of an image distortion compensation device, 100", which further includes a storage unit. Device 100" includes a storage unit 140 to store spectral characteristics of the safety goggles.

As described above, the type of safety goggles is changed according to the wavelength region of a laser irradiated to the medical imaging device 50. The safety goggles may be categorized according to spectral characteristics thereof and each pair of safety goggles has inherent spectral characteristics. Absorbance according to light wavelengths may be used as the spectral characteristic of the safety goggles; however, other properties can be alternatively or additionally accounted for in other embodiments of the present invention.

The storage unit 140 stores information on the safety goggles and spectral characteristics corresponding thereto. In an embodiment, when names to distinguish safety goggles and spectral characteristics corresponding thereto are databased, the user is prompted to select a name of the safety goggles used. This eliminates an operation step of inputting spectral characteristics of the safety goggles whenever the medical imaging device 50 is used. User selection may be carried out through the input unit of the medical imaging device 50.

Figure 12A:
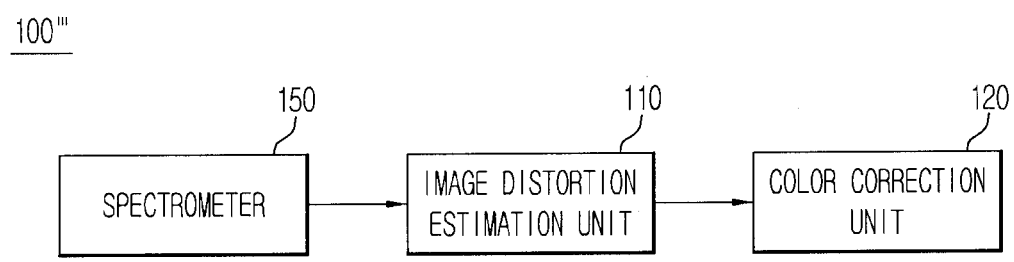
FIGS. 12A and 12B are block diagrams illustrating respective configurations of an image distortion compensation device further including a spectrometer.
Figure 12B:
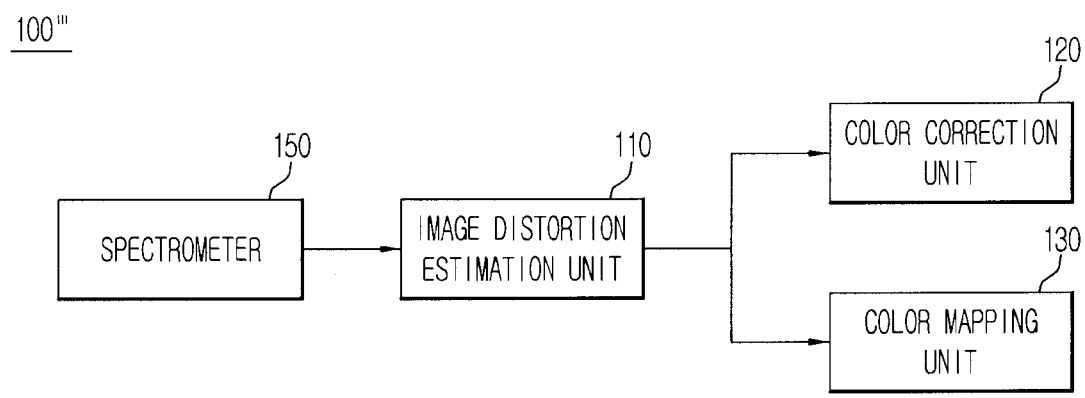

FIGS. 12A and 12B are block diagrams illustrating respective configurations of an image distortion compensation device, 100''', further including a spectrometer.

In the embodiments described with reference to FIGS. 11A and 11B, the image distortion compensation device 100" includes the storage unit 140 to store spectral characteristics of the safety goggles, whereas the image distortion compensation device 100''' includes a spectrometer 150 to measure spectral characteristics.

The spectrometer 150 measures spectral characteristics of the safety goggles, allows spectral characteristics of safety goggles to be automatically input to the image distortion estimation unit 110 and enables compensation of image distortion, without the need for the user to input spectral characteristics or a name of the safety goggles. Also, the spectrometer 150 measures spectral characteristics of the display unit and inputs the measurement results to the image distortion estimation unit 110.

Hereinafter, a medical imaging device including the image distortion compensation device described above will be described below.

Figure 13:
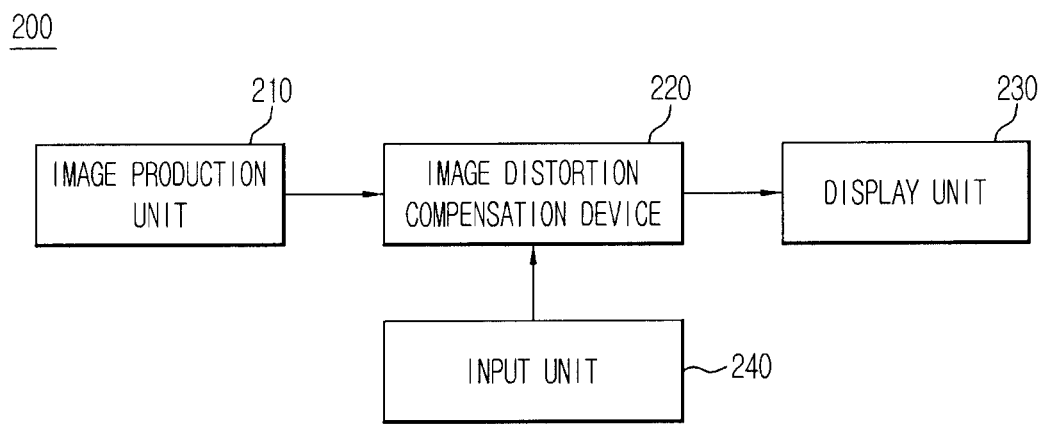
FIG. 13 is a block diagram illustrating a configuration of a medical imaging device according to one embodiment of the present invention.

FIG. 13 is a block diagram illustrating a configuration a medical imaging device, 200, according to one embodiment of the present invention. Medical imaging device 200 includes an image production unit 210 to produce a medical image of an object, an image distortion compensation device 220 to compensate image distortion generated during wearing of the safety goggles, a display unit 230 to display the compensated image and an input unit 240 to receive user selection.

In the normal use of medical imaging device 200, the user wears safety goggles to block light of a specific wavelength region in order to perceive compensated images of the object. Representative examples of medical imaging device 200 include a photoacoustic imaging device emitting a laser with a short wavelength to obtain images of the object, and a photoacoustic/ultrasonic imaging device in which a photoacoustic imaging device is combined with an ultrasonic imaging device. Other types of imaging devices are also possible. Any medical imaging device may be applied to the embodiments of the present invention so long as its use requires, recommends or permits goggles absorbing light of a specific wavelength region be worn.

The image production unit 210 may produce an image of an object, produce a black-and-white image according to the application thereof and the diagnosis site of the object and/or produce a color image.

The display unit 230 displays an image produced by the image production unit 210, which is image compensated by the image distortion compensation device 100, and is realized with a CRT, LCD, LED, PDP or the like. Spectral characteristics of the display unit 230 depend on the type thereof.

The image distortion compensation device 220 compensates an image which is produced by the image production unit 210 and then displayed on the display unit 230. Thereby, it prevents the image from being perceived distorted when viewed using the safety goggles.

The image distortion compensation device 220 is the same as the image distortion compensation devices 100, 100', 100" or 100''' of the embodiments described in FIGS. 3 to 11. Accordingly, the image distortion compensation device 220 includes the image distortion estimation unit 110 and the color correction unit 120 and further includes at least one of the color mapping unit 130, the storage unit 140 and the spectrometer 150.

The image distortion compensation device 220 may be mounted in a host device of the medical imaging device 200 and operated by a controller such as a CPU or MCU present in the host device.

Specifically, the image compensated by the image distortion compensation device 220 is displayed on the display unit 230. When color correction is impossible through the color correction unit 120, the impossibility and the alternative color are informed to the user through the display unit 230.

Also, the input unit 240 may receive a selection of the alternative color to be mapped in the color mapping unit 130, or selection of the safety goggles may be input through the input unit 240, in a case where the image distortion compensation device 220 further includes the storage unit 140.

Further, input unit 240 may receive a selection regarding wearing of safety goggles. According to the selection received by the input unit 240, when the user wears the safety goggles, a color-corrected image is displayed, and when the user does not wear the safety goggles, a non-color-corrected image is displayed.

Figure 14:
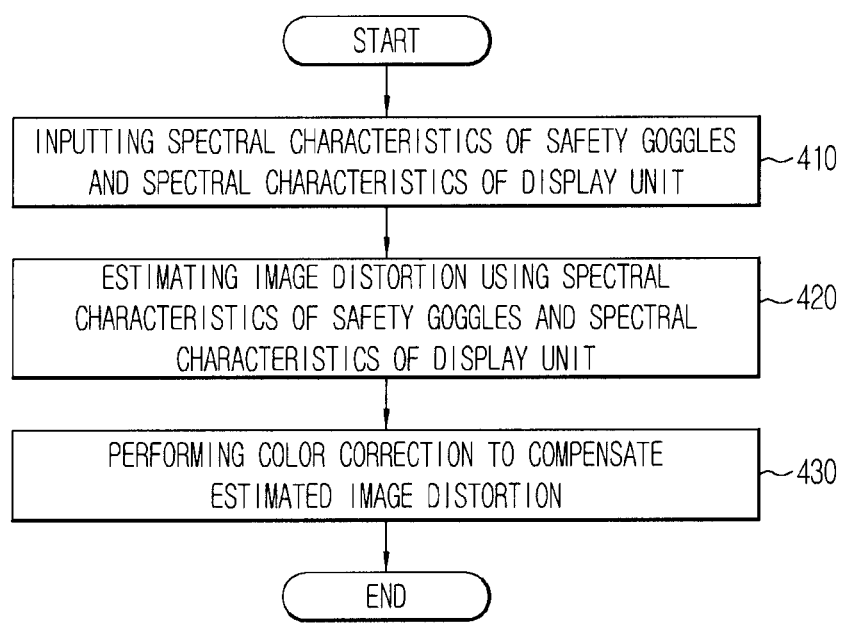
FIG. 14 is a flowchart illustrating a method for compensating image distortion according to one embodiment of the present invention.

FIG. 14 is a flowchart illustrating a method for compensating image distortion according to one embodiment of the present invention. Initially, spectral characteristics of safety goggles and spectral characteristics of the display unit are input (410). These characteristics may be directly input from the user or a designer, or values measured by the spectrometer may be input. The safety goggles and the display unit have inherent spectral characteristics; the spectral characteristics used for the safety goggles may be light absorbance according to wavelength.

Next, image distortion is estimated using the spectral characteristics of the safety goggles and of the display unit (420). Here, estimated image distortion means an estimate of image distortion generated when the image displayed on the display unit traverses the safety goggles, i.e., distortion observable by a user wearing the glasses. The image distortion may be generally estimated by calculating change in coordinate of at least one of the three primary colors caused by light absorption by the safety goggles and thus change in coordinate of a specific color. A detailed description of the method for estimating image distortion is given in the above-described embodiments and is thus omitted in the present discussion.

Next, color correction to compensate the estimated image distortion is performed (430). Specifically, an additive synthesis ratio is adjusted such that a specific color is created by combining three primary colors having changed coordinates.

When the color-corrected image is displayed through the display unit, image distortion as perceived by the user wearing the goggles is reduced or eliminated.

The embodiment of FIG. 14 may be applied to compensation of black-and-white images as well as compensation of color images.

Figure 15:
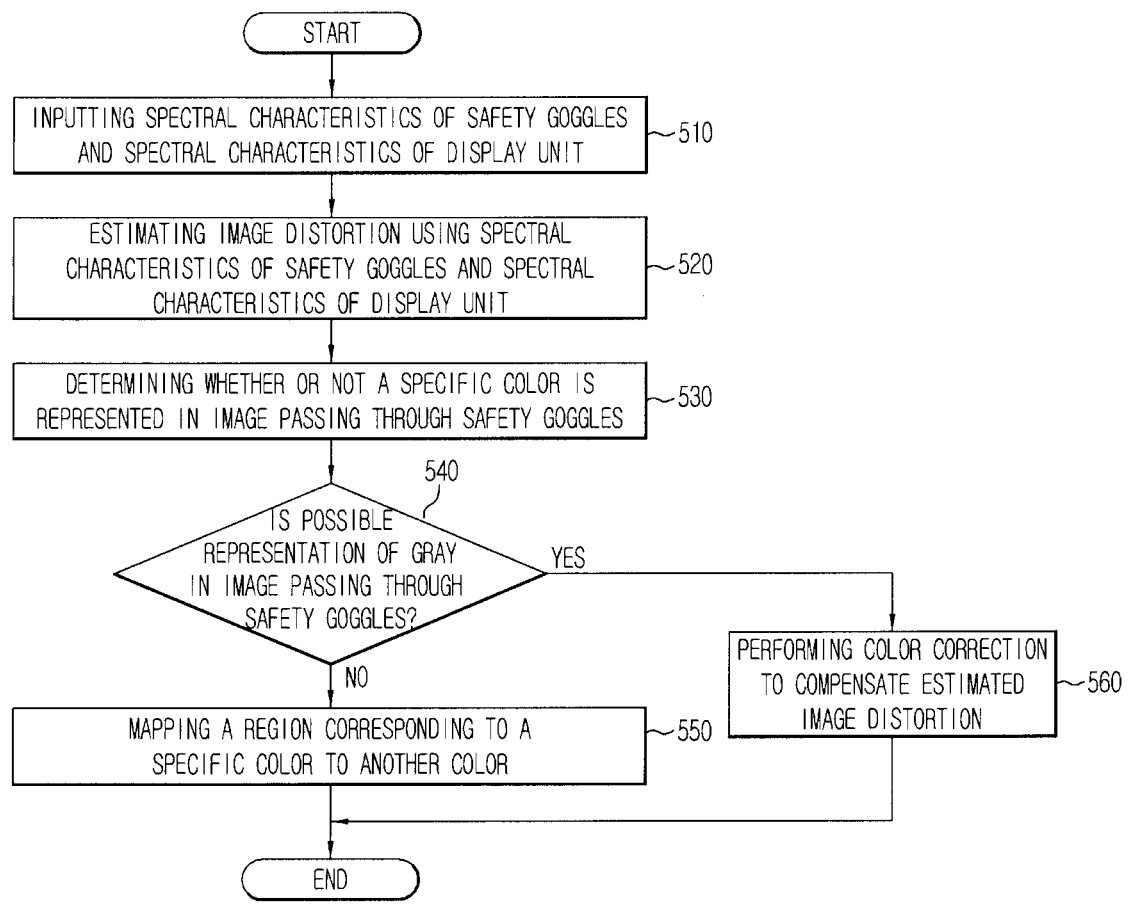
FIG. 15 is a flowchart illustrating a method for compensating image distortion applicable to a case in which color correction is impossible.

FIG. 15 is a flowchart illustrating a method for compensating image distortion applicable to a case in which color correction is impossible. Here, spectral characteristics of the safety goggles and spectral characteristics of the display unit are input (510), and image distortion is estimated using the input spectral characteristics (520).

As a result of the estimation, whether or not a specific color is represented in the image traversing (passing through) the safety goggles is determined (530). Specifically, when the image displayed on the display unit is a black-and-white image, whether or not gray is represented in the image traversing the safety goggles is determined and when the image displayed on the display unit is a color image, whether or not a specific color not represented in the image traversing the safety goggles is present is determined.

In an embodiment, in a case where the image displayed on the display unit is a black-and-white image, when applying light absorption properties of the safety goggles, a gray coordinate is present in the color gamut created by the changed coordinates of three primary colors, representation of gray on the image traversing the safety goggles is determined to be possible, and when the gray coordinate is not present in the color gamut, representation of gray on the image traversing the safety goggles is determined to be impossible.

When representation of gray on the image passing through the safety goggles is possible, (Yes of 540), color correction to compensate the estimated image distortion is performed (560).

When representation of gray on the image traversing the safety goggles is impossible, (No of 540), a region corresponding to a specific color is mapped to another color (550). Specifically, when the image displayed on the display unit is a black-and-white image, a color other than gray is mapped, brightness thereof is controlled, and intended information of the black-and-white image is displayed. When the image displayed on the display unit is a color image, a region corresponding to a specific color not represented in the image traversing the safety goggles is mapped to other color and the image is displayed on the display unit.

Also, when representation of a specific color on the image passing through the safety goggles is impossible, the user is informed of such impossibility so as to enable the user to prepare for image distortion and allow the user to select an alternative color. When another color is arbitrarily mapped, the user is informed of the mapped color to enable the user to analyze the image without difficulty and confusion.

As apparent from the foregoing, at least some embodiments of the present invention provide an image distortion compensation device which enables a user/inspector to perceive a medical image having reduced or eliminated image while wearing color-filtered safety goggles, by correcting colors of a medical image displayed on a display unit using spectral characteristics of the safety goggles. Medical imaging devices including the same and method for compensating image distortion have also been disclosed.

The above-described methods according to the present invention can be implemented in hardware, firmware or as software or computer code that can be stored in a recording medium such as a CD ROM, an RAM, a floppy disk, a hard disk, or a magneto-optical disk or computer code downloaded over a network originally stored on a remote recording medium or a non-transitory machine readable medium and to be stored on a local recording medium, so that the methods described herein can be rendered in such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein.

Although several embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An image distortion compensation device for compensating image distortion on image traversing safety goggles comprising:
   an image distortion estimation unit to preliminarily estimate image distortion based on spectral characteristics of the safety goggles; and
   a color correction unit to perform color correction to compensate the estimated image distortion with respect to an image to be displayed on a display unit; and
   wherein the spectral characteristics of the safety goggles comprise light absorbance of the safety goggles according to wavelength, wherein the image distortion estimation unit determines whether or not compensation of image distortion is possible through the color correction, wherein the image distortion estimation unit determines that compensation of the image distortion is impossible through the color correction when, among colors used for the image to be displayed on the display unit, a color not represented in the image to be displayed on the display unit to which light absorption effects of the safety goggles are applied is present.

2. The image distortion compensation device according to claim 1, wherein the image distortion estimation unit estimates image distortion by applying absorption effects of the safety goggles to the image to be displayed on the display unit using the spectral characteristics of the safety goggles.

3. The image distortion compensation device according to claim 1, further comprising a color mapping unit to substitute the color not represented in the image to which light absorption effects of the safety goggles, among the colors used for the image displayed on the display unit, by a color represented in the image to which light absorption effects of the safety goggles are applied.

4. The image distortion compensation device according to claim 1, further comprising a storage unit to store at least one spectral characteristic of the safety goggles.

5. The image distortion compensation device according to claim 4, wherein the image distortion estimation unit estimates image distortion using a selected one or more of the at least one spectral characteristics stored in the storage unit.

6. The image distortion compensation device according to claim 4, further comprising:
   a user input unit for receiving user inputs of the at least one spectral characteristic of the safety goggles.

7. The image distortion compensation device according to claim 4, wherein the storage unit stores at least one spectral characteristic of a plurality of safety goggles, said plurality of safety goggles comprises the safety goggles;
   a user input device configured to receive a user selection of a selected one of the plurality of safety goggles; and
   wherein the image distortion estimation unit is configured to estimate image distortion based on the spectral characteristics of the safety goggles, wherein the spectral characteristics of the safety goggles further comprise spectral characteristics of the selected one of the plurality of safety goggles.

8. The image distortion compensation device according to claim 1, wherein the image distortion estimation unit estimates coordinate change of primary colors by absorption properties of the safety goggles, thereby resulting in estimated coordinates of the primary colors, and wherein the estimated coordinates of the primary colors comprise coordinates in a color space used for the display unit.

9. The image distortion compensation device according to claim 8, wherein the color correction unit controls a synthesis ratio of the primary colors to realize a specific color included in the image displayed on the display unit, based on the estimated coordinates of the primary colors.

10. The image distortion compensation device according to claim 1, further comprising a spectrometer to measure the spectral characteristics of the safety goggles.

11. The image distortion compensation device of claim 1, wherein the image distortion estimation unit determines a gamut coordinate for at least one primary color for the display unit, based on the spectral characteristics of the goggles.

12. The image distortion compensation device of claim 1, further comprising:
   the display unit configured to display the image to be displayed; and
   wherein the image distortion estimation unit is configured to preliminarily estimate image distortion based on the spectral characteristics prior to the display unit displaying the image.

13. A medical imaging device comprising the image distortion compensation device according to claim 1.

14. The medical imaging device according to claim 13, wherein the medical imaging device comprises the display unit, wherein the display unit displays a photoacoustic image or a photoacoustic/ultrasonic image of an object.

15. The medical imaging device according to claim 14, wherein the display unit displays an image color-corrected by the color correction unit or an image color-mapped by a color mapping unit.

16. The medical imaging device according to claim 14, further comprising an input unit to receive a selection of a substituted color from a color mapping unit.

17. The medical imaging device according to claim 14, further comprising an input unit to receive a selection of at least one of spectral characteristics of the safety goggles stored in a storage unit.

18. A method for compensating image distortion generated in an image passing through safety goggles, the method comprising:
   estimating the image distortion based on spectral characteristics of the safety goggles; and
   performing color correction to compensate the estimated image distortion with respect to an image to be displayed on a display unit; and
   wherein the spectral characteristics of the safety goggles comprise light absorbance of the safety goggles according to wavelength, wherein the estimation of image distortion is carried out by applying absorption effects of the safety goggles to the image to be displayed on the display unit using the spectral characteristics of the safety goggles, the method further comprising:
   determining whether or not compensation of image distortion is possible through color correction, wherein the determining whether or not compensation of image distortion is possible through color correction comprises determining that compensation of the image distortion is impossible through color correction when, among colors used for the image to be displayed on the display unit, a color not represented in the image to be displayed on the display unit to which light absorption effects of the safety goggles are applied is present.

19. The method according to claim 18, wherein the estimation of the image distortion comprises estimating coordinate change of primary colors through absorption effects of the safety goggles, thereby resulting in estimated coordinates of the primary colors,
   wherein the estimated coordinates of the primary colors comprise coordinates in a color space used for the display unit.

20. The method according to claim 19, wherein the color correction comprises controlling a synthesis ratio of the primary colors to realize a specific color included in the image to be displayed on the display unit, based on the estimated coordinates of the primary colors.

21. The method according to claim 18, further comprising:
   substituting the color not represented in the image to which light absorption effects of the safety goggles are applied, among the colors used for the image displayed on the display unit, by a color represented in the image to which light absorption effects of the safety goggles are applied.

22. The method according to claim 21, wherein the spectral characteristics of the safety goggles used for estimation of the image distortion comprise a selected spectral characteristics of the safety goggles.

23. The method according to claim 18, further comprising:
   storing at least one spectral characteristic of the safety goggles; and
   receiving selection of at least one of the spectral characteristics of the safety goggles stored in a storage unit.

24. A non-transitory computer-readable storage medium having stored therein program instructions, which when executed by a computer, perform the method of claim 18.

* * * * *